United States Patent [19]

Downer et al.

[11] 4,125,400

[45] Nov. 14, 1978

[54] AGRICULTURAL SPRAY OIL CONTAINING OXIDATION INHIBITORS

[75] Inventors: John D. Downer; Clarence A. L. Phillips, both of Pointe-a-Pierre, Trinidad and Tobago

[73] Assignee: Texaco Trinidad, Inc., Pointe-a-Pierre, Trinidad and Tobago

[21] Appl. No.: 835,280

[22] Filed: Sep. 21, 1977

[51] Int. Cl.$^2$ .............................................. A01N 17/08
[52] U.S. Cl. .................................. 71/127; 71/DIG. 1; 71/122; 424/358
[58] Field of Search ................... 71/122, 127, DIG. 1; 424/358

[56] References Cited

U.S. PATENT DOCUMENTS 3,097,088  7/1963  Reck et al. ............................... 71/127

OTHER PUBLICATIONS

Tucker., Ind. Eng. Chem., vol. 28, (1936) 458.

*Primary Examiner*—Catherine L. Mills
*Attorney, Agent, or Firm*—Thomas H. Whaley; Carl G. Ries; Henry W. Archer

[57] ABSTRACT

The phytotoxicity of petroleum spray oils can be eliminated or reduced by the addition thereto of from 0.01 to 8% weight percent of an antioxidant of the inhibitor or peroxide decomposing type, which is non-phytotoxic, non-carcinogenic and substantially unaffected in its antioxidant properties by sunlight. These inhibitors prevent the auto-oxidation of the oils.

5 Claims, No Drawings

4,125,400

AGRICULTURAL SPRAY OIL CONTAINING OXIDATION INHIBITORS

BACKGROUND OF THE INVENTION

1. Field of the Invention

This invention relates to reducing the phytotoxicity of conventional horticultural petroleum spray oils. More specifically, the invention relates to the incorporation in such oils of auto-oxidation inhibitors which are themselves non-phytotoxic non-carcinogenic and safe for use on crop. In particular, the invention is directed to preventing oxidation of spray oils which are exposed to strong sunlight over a protracted length of time.

Petroleum oils are used in agriculture as carriers or solvents for spraying pesticides (fungicides, insecticides, ovicides, etc.), herbicides, micronutrients and various types of chemical adjuvants. They are also used as agricultural spray oils in their own right, i.e., without additives, because of their natural herbicidal and pesticidal properties. They control a wide range of pests, for examples, Sigatoka disease in banana, earworm in sweet corn, Cercospora in sugar beet, and mites, aphids, scale insects in decideous fruit trees, citrus and ornamentals. The main advantage of petroleum spray oils are their relative cheapness, their low health hazard and the apparent inability of fungi, insects and mites to develop strains resistant to them.

The properties required for an oil to perform efficiently as a carrier do not necessarily conflict with those required for an oil to act as a natural herbicidal or pesticidal spray oil. Indeed many commercial spray oils perform both functions. Present day conventional petroleum spray oils are derived from light lube oil distillates.

The horticultural spray oils have a gravity API of 31-36, a viscosity at 100° F. of 81 to 87 Saybolt Universal Seconds and a boiling range between 600° and 775° F. An analysis of four preferred oils samples is given in Table I. For normal applications highly refined carrier oils, predominantly paraffinic, having a minimum API gravity of 27, viscosity at 100° F. of between 55 and 100 Saybolt Universal Seconds, boiling range of 600°-775° F. and minimum unsulphonated residue of 85%, are generally used. A lighter oil with API gravity around 50 and boiling point range 85°-600° F. belonging to the general groups of paraffins, isoparaffins and/or naphthenes is desirable for use with light-weight ultra low volume sprayers.

TABLE I

| ANALYSES OF CARRIER OILS USED | | | | |
|---|---|---|---|---|
| | Carrier Oil Samples | | | |
| | RS-1200/67 | RS-932/67 | RS-175/60 | RS-370/71 |
| Specific Gravity at 60/60° F (ASTM D-1298) | 0.8493 | 0.8487 | 0.8523 | 0.8492 |
| Gravity, ° API (ASTM D-1250) | 35.1 | 35.2 | 34.5 | 35.1 |
| Flash Point (COC), ° F (ASTM D-92) | 395 | 395 | 405 | 395 |
| Viscosity at 100° F SUS (ASTM D-445/2161) | 84.2 | 83.3 | 86.5 | 81.6 |
| Color (ASTM D-1500) | <0.5 | 0.5 | 0.5 | 0.5 |
| Pour Point, ° F (ASTM D-97) | 5 | 5 | 20 | 5 |
| Ash, wt. % | Trace | Trace | 0.003 | 0.005 |
| Corrosion Copper Strip 3 hrs. at 212° F (ASTM D-130) | Pass | Pass | 1A | 1A |
| Neutralization Number mg. KOH/g | 0.04 | 0.09 | 0.054 | 0.044 |
| Unsulfonated Residue, vol. % (ASTM D-483) | 94.2 | 94 | 92.8 | 91.4 |

TABLE I-continued

| ANALYSES OF CARRIER OILS USED | | | | |
|---|---|---|---|---|
| | Carrier Oil Samples | | | |
| | RS-1200/67 | RS-932/67 | RS-175/60 | RS-370/71 |
| Distillation, ° F | | | | |
| IBP | 637 | 649 | 649 | 610 |
| 10% Recovery | 675 | 685 | 674 | 671 |
| 90% Recovery | 729 | 730 | 729 | 732 |
| FBP | 745 | — | 750 | 756 |

Physical data for a typical spray oil are given in Table I. There is a definite relationship between the unsaturates (aliphatic or cyclic hydrocarbons that have one or more active double or triple bonds) content of petroleum oils and phytotoxicity or leaf burn. It has been established that the aromatic hydrocarbon components are indirectly responsible for leaf injury. Thus R. P. Tucker (Ind. Eng.Chem., 1936, 28, 458) has shown that the aromatic hydrocarbons are not toxic to the foilage of plants in a chemical sense until they are oxidized to oil soluble asphaltogenic acids. Saturated hydrocarbon components are also oxidized to acid material. However, the rate of oxidation of the saturates at ordinary temperatures is so slow that they are chemically inert towards foliage. The real causes of phytotoxicity have yet to be determined; it is believed that there is both a chemical action and a physical one. The tendency of the unsaturated hydrocarbons to oxidize to asphaltogenic acids is undoubtedly the principal non-physical factor involved in phytotoxicity. It is a fact that conventional spray oils low in aromatic hydrocarbons are relatively non-phytotoxic.

In understanding the present invention it should be remembered that the unsulfonated residue (UR) content of a conventional petroleum spray oil is a measure of the degree of refinement, ie. the absence of aromatics which directly or indirectly cause leaf burn and fruit blotch. Petroleum spray oils are refined by extraction of the aromatics with solvents, e.g., furfural, or by reaction with sulphuric acid. The UR content of an oil is determined by ASTM D 483 which gives an approximate content of the saturated hydrocarbons present by measuring the percent unreactive to 37N sulphuric acid. Light mineral oils with UR levels in the range 70-100 are equally effective in disease control. However, the degree of leaf damage is related to the UR level. In a similar boiling range, oils with the highest UR level cause the least damage. Location may also be a factor. Thus citrus trees are not so adversely affected by an oil of low UR level in more humid regions. A relatively safe level of UR is 92% indicating the percentage of non-aromatic hydrocarbon components in the oil.

The rate of autoxidation of oils containing an appreciable amount of unsaturated hydrocarbons and aromatics, i.e., relatively low UR level, is very slow in the absence of light but sunlight activates the oxidation to a marked degree forming the toxic asphaltogenic acids. The amount of acid injurious to foliage is relatively small.

SUMMARY OF THE INVENTION

It has been discovered that the phytotoxicity of petroleum spray oils can be eliminated or reduced by the addition of an antioxidant, preferably of the inhibitor type, such as amines, hindered phenols, aminophenols, etc., and the peroxide decomposing type, such as thiocarbamates. The antioxidant must be non-phytotoxic, non-carcinogenic and its antioxidant properties must be substantially unaffected by sunlight. From 0.01 to 8 weight percent of the additives are incorporated in the oils.

DISCLOSURE OF THE INVENTION

Certain antioxidants such as $\beta$-naphthylamine are recognized carcinogens and although they might be effective in reducing leaf burn, such additives would not be desirable for use in spraying food crops. Preferred additives are various food antioxidants and in particular the hindered phenols, e.g., BHA and BHT, which are already known to be non-carcinogenic.

Before demonstrating the beneficial effects of using antioxidants for reducing the phytotoxicity of conventional petroleum spray oils, experiments were made to demonstrate the formation of asphaltogenic acids, and the effect of various antioxidants in inhibiting the formation of these acids in spray oils with different UR contents. The general procedure used for these experiments is described in Example I and the results given in Tables II and III. The results confirm the formation of acids in the oil when exposed to sunlight. The spray oils used had zero acid value. It will be seen from Tables II and III that the oils without antioxidant developed an appreciable acid value after they had been dispersed and exposed to sunlight over 21 days; whereas the unexposed dispersed oils used as control did not develop an acid value after storing in the dark for 21 days. Acid formation on exposure to sunlight appears to increase as the UR content of the spray oil decreases (Table III). It is also very apparent that the amount of acids formed is appreciably reduced when antioxidant is added to the spray oil. Table II lists the antioxidants examined in order of effectiveness in inhibiting autoxidation of the oil, the most effective being the amine type.

In evaluating the additives of this invention, it was necessary to check on the phytotoxicity of the antioxidants themselves. For this purpose a greenhouse trial was made on corn seedlings with a number of commercial antioxidants carried in alkylate bottoms, a non-phytotoxic light aliphatic hydrocarbon mixture. Details of the trial are described in Example II and the overall phytotoxicity score is given in Table IV. The results showed that the level of phytotoxicity of many of the antioxidants, including those generally recognized as safe for food production, is only slight, even at the relatively high concentration of 0.28% w/v used for an antioxidant. In view of the low phytotoxicity exhibited by many antioxidants there is a very good chance of being able to show the beneficial effect to plant growth when an antioxidant is added to a conventional spray oil. Two experiments are described.

Antioxidants representative of four important classes of antioxidants were added to two spray oils of different UR contents (84 and 95%) at a relatively low concentration, and applied to corn seedlings to demonstrate the beneficial effects on growth which their presence imparts to the spray oil. The procedure used and the results obtained are given in Example III and Table V. On this basis, the variance (F) ratio, the treatment effects on the mean seedling fresh weight, the mean functional leaf area, the mean total leaf area and the mean phytotoxicity rating were all significant. Using as a basis the standard error of difference between treatment means, the mean treatment effects on the other parameters measured were also significant. The mean functional and total leaf areas and the mean number of leaves produced by seedlings treated with Oil A (84% UR) containing 2-4-dimethyl-6-tert. butylphenol were significantly greater than those of seedlings treated with the neat oil. The mean fresh weight of seedlings treated with oil A containing 2-mercaptobenzothiazole and that of the number of leaves of plants treated with oil A containing zinc dibutyldithiocarbamate were significantly greater than those of plants receiving the neat oil. In oil B (95% UR), the effect of each of the antioxidants appears to be even greater. The mean functional and total leaf areas and the mean fresh weight of seedlings treated with oil B containing separately 2,4-dimethyl-6-tert. butylphenol, 2-mercaptobenzothiazole, zinc dibutyldithiocarbamate or the sulfurized sperm oil, were significantly greater than those treated with only oil. Also the dry weight of seedlings treated with oil B containing 2-mercaptobenzothiazore, zinc dibutyldithiocarbamate or sulfurized sperm oil were significantly greater than that of seedlings smeared with the neat oil.

In a further experiment to demonstrate the beneficial effect on plant growth when an oxidation inhibitor is added to the spray oil, an antioxidant (mixed alkylphenols) was used at various concentrations in four spray oils of different UR contents. The procedure used and the results obtained are given in Example IV and Table VI. Basis the variance (F) ratio, the effect of the antioxidant concentration in the spray oil of 84 and 95% UR content had a significant effect on all parameters measured, except that the nonfunctional leaf area. In both spray oils, the growth of corn seedlings was optimum at antioxidant contents up to about 2%. The effect on seedling growth of the antioxidant concentration in the spray oils of 60 and 72% UR content was not significant for all the parameters measured. However, there was a marked trend of improved seedling growth with increased antioxidant content of the spray oil. It would seem that the lower the UR content of the spray oil the higher must the antioxidant concentration be for proper seedling growth.

Examples of data supporting the invention and evaluations of the data are presented below.

EXAMPLE I

General procedure for determining the effectiveness of anti-oxidants in inhibiting autoxidation of spray oils.

The spray oil with or without antioxidant was absorbed on glass wool and placed in a glass dish. This was left to stand in a greenhouse exposed to the atmosphere at ambient temperature, 30° C. After 21 days the oil was extracted from the glass wool with solvent by Soxhlet extraction, the solvent stripped from the extract and the acid value of the residual oil determined. The results given in Table II indicate, in order of effectiveness, the inhibition of autoxidation achieved by addition of various antioxidants (at 0.25% w/v) to a spray oil of 84% unsulphonated residue (UR) content. The results given in Table III show the effectiveness of antioxidants in inhibiting autoxidation of spray oils of varying UR contents, 60, 72, 84 and 95%.

EXAMPLE II

Phytotoxicity of Various Antioxidants

The antioxidants listed in Table IV were carried at 0.25% w/v in alkylate bottoms. Corn seedlings, grown in a mixture of vemiculite/peat moss/sand/charcoal medium contained in plastic pots in a greenhouse were used as the trial crop. The trial was of a randomized block design with 13 treatments replicated 3 times in three blocks. Two controls, an untreated and that of alkylate bottoms were included. The carrier and the solutions were applied twice to the seedlings by smearing the ventral side of the leaves using cotton wool soaked in the solutions. The first smear was applied 7 days after the seedlings emerged, and the second seven days later. The extent of leaf burn caused by the treatments was assessed two days after treatment. The plants were measured and harvested to determine fresh and dry tissue weights seven days after the second smear treatment. The overall phytotoxicity score is shown in Table IV with the antioxidants of lower phytotoxicity ranking highest.

EXAMPLE III

Beneficial Effect of Antioxidants on Spray Oil Phytotoxicity

Corn seedlings grown in a greenhouse in a mixture of vermiculite, peat moss, sand and charcoal contained in plastic pots were used as the test crop. A randomized block design was used with eleven treatments replicated three times in three blocks. The antioxidants, given in Table V, were added to each of two spray oils A and B (UR contents of 84 and 95% respectively) at 0.1% wt./vol. concentration giving eight treatments in addition to the two oils alone and an unsprayed control. The oils and/or oil solutions were applied twice to the seedlings by smearing the underside of the leaves with oil-soaked cotton wool. The first treatment was given seven days after the seeds were sown and the second one seven days after the first; only newly emerged leaves were smeared during the second application. The seedlings were assessed for leaf damage the day after applying the treatments and were allowed to grow for a further 7 days after the second treatments before measuring and harvesting for tissue weight determination. The results, given in Table V, indicate that the growth of seedlings treated with antioxidant is significantly greater than that treated with spray oil alone.

EXAMPLE IV

Relationship Between Antioxidant Concentration And Unsulfonated Residue Content of the Spray Oil Mixed alkylphenols containing 55%, 2,4-dimethyl-6-tert. butylphenol, at five concentrations, 0, 1, 2, 4 and 8% wt. were blended in factorial combination with conventional type spray oils (see Table I) of varying UR contents, viz. 95, 84, 72 and 60%. Two separate factorially designed greenhouse trials with ten treatments running concurrently were made using corn seedlings grown in peat moss/soil/sand/charcoal mixed medium contained in plastic pots. Each experimental unit consisted of a single pot in which the three seedlings were grown. The treatments were applied once to the underside of the leaves of 7-day old seedlings by smearing cotton wool steeped in the solution. The treatments were replicated three times in three blocks. The plants grew for 14 days after treatment before measuring and harvesting for determining fresh and dry tissue weights. The results are given in Table IV and show a marked trend of improved seedling growth with increased antioxidant concentration in the spray oils. It is also apparent that the lower the UR content of the spray oil the higher must the antioxidant concentration be for proper seedling growth.

TABLE II

EFFECTIVENESS OF ANTIOXIDANTS IN INHIBITING AUTOXIDATION OF SPRAY OIL, 84% UR

| | Acid Value, mg.KOH/g. (after exposure to sunlight for 21 days) |
|---|---|
| N,N'-Di-sec. butyl-p-phenylenediamine | 0.26 |
| Phenyl-α-naphthylamine | 0.27 |
| Sulfurized sperm oil | 0.76 |
| p,p'-Dioctyldiphenylamine | 0.98 |
| 4-Methyl-2,6-di-tert. butylphenol | 1.09 |
| 2-Mercaptobenzothiazole | 1.17 |
| 2,4-Dimethyl-6-tert. butylphenol | 1.23 |
| Mixed alkylphenols containing 55% 2,4-dimethyl-6-tert. butylphenol | 1.28 |
| Zinc dibutyldithiocarbamate | 1.29 |
| None[a] (spray oil alone) | 2.8 |

[a]The acid value of an unexposed sample of spray oil alone was zero.

TABLE III

EFFECTIVENESS OF ANTIOXIDANTS IN INHIBITING AUTOXIDATION OF SPRAY OILS OF DIFFERENT UR CONTENTS

| | Acid Value, mg KOH/g., after exposure to sunlight for 21 days | | | |
|---|---|---|---|---|
| Antioxidant, 0.25% wt./vol. | 60% UR Oil | 72% UR Oil | 84% UR Oil | 95% UR Oil |
| N,N'-Di-sec. butyl-p-phenylenediamine | 0.18 | 0.18 | 0.10 | 0.07 |
| Phenyl-α-naphthylamine | 0.78 | 0.60 | 1.15 | 0.27 |
| 2,4-Dimethyl-6-tert. butylphenol | 0.81 | 0.76 | 0.55 | 0.42 |
| Mixed alkylphenols containing 55% 2,4-dimethyl-6-tert. butylphenol | 1.25 | 0.96 | 0.92 | 0.47 |
| Sulfurized sperm oil | 1.68 | 1.66 | 0.47 | 0.80 |
| 4-Methyl-2,6-di-tert. butylphenol | 1.48 | 2.07 | 3.50 | 1.30 |
| None[a] (spray oil alone) | 2.0 | 2.8 | 4.8 | 3.8 |

[a]The Acid value of the unexposed oils were zero in every case.

TABLE IV

ANTIOXIDANT PHYTOTOXICITY TRIAL

| | Phytotoxicity Score* |
|---|---|
| Alkylate Bottoms | 0.1a** |
| Control (untreated) | 0.0a |
| Diphenylamine | 0.0a |
| Mixed alkylphenols*** | 0.2a |
| β-Naphthylamine | 0.3a |
| 2-Mercaptobenzothiazole | 1.0bc |
| p,p'Dioctyldiphenylamine | 1.2bc |
| 2,4-Dimethyl-6-tert. butylphenol | 1.3bcd |
| Sulphurized sperm oil | 0.9b |
| 4-Methyl-2,6-ditert. butylphenol | 1.3bcd |
| N,N'-Di-sec. butyl-p-phenylenediamine | 1.4cd |
| Zinc dibutyldithiocarbamate | 1.7d |
| Phenyl-α-naphthylamine | 1.1cd |

*Phytotoxicity score: 0 = none; 1 = slight; 2 = moderate; 3 = severe.
**Figures followed by the same letter are not significantly different (5% level).
***Contains 55% 2,4-dimethyl-6-tert. butylphenol.

TABLE V

PHYTOTOXICITY OF SPRAY OILS CONTAINING ANTIOXIDANTS: MEAN TREATMENT EFFECT ON SEEDLING CORN

| Treatment (0.1% Antioxidant) | Height cm. | Weight in gms. Fresh | Weight in gms. Dry | No. of Leaves | Leaf Area, (cm$^2$) Non-functional | Leaf Area, (cm$^2$) Functional | Leaf Area, (cm$^2$) Total | Phytotoxicity Score[a] |
|---|---|---|---|---|---|---|---|---|
| Control | 17.5 | 14.4 | 1.57 | 16.0 | 38.4 | 1405.7 | 1444.0 | 0.3 |
| Oil A (84% UR) alone | 15.6 | 5.4 | 1.00 | 12.7 | 68.0 | 712.7 | 780.6 | 1.4 |
| Oil B (95% UR) alone | 14.9 | 8.9 | 0.83 | 15.0 | 35.8 | 942.0 | 977.7 | 0.9 |
| 2,4-Dimethyl-6-tert. butylphenol in A | 16.3 | 6.2 | 1.30 | 15.3 | 51.1 | 962.5 | 1013.6 | 1.4 |
| 2,4-Dimethyl-6-tert. butylphenol in B | 17.9 | 11.3 | 1.23 | 15.7 | 45.3 | 1180.1 | 1225.4 | 1.5 |
| 2-Mercaptobenzothiazole in A | 15.4 | 7.8 | 1.07 | 15.0 | 65.7 | 846.8 | 912.6 | 1.4 |
| 2-Mercaptobenzothiazole in B | 17.3 | 12.3 | 1.33 | 15.3 | 26.9 | 1197.1 | 1224.0 | 1.4 |
| Zinc dibutyldithiocarbamate in A | 13.3 | 6.6 | 1.00 | 14.0 | 32.5 | 776.2 | 808.7 | 1.4 |
| Zinc dibutyldithiocarbamate in B | 16.6 | 12.5 | 1.37 | 15.7 | 35.5 | 1279.1 | 1314.7 | 0.9 |
| Sulfurized sperm oil in A | 13.2 | 6.6 | 1.33 | 13.0 | 90.4 | 676.3 | 766.7 | 1.2 |
| Sulfurized sperm oil in B | 17.6 | 11.4 | 1.50 | 15.3 | 51.7 | 1166.7 | 1218.4 | 0.7 |
| S.E. $\phi$ | 1.62 | 1.68 | 0.329 | 0.88 | 19.66 | 147.26 | 142.27 | 0.25 |
| C.V. % | 17.6 | 31.0 | 46.33 | 10.3 | 69.2 | 25.2 | 23.19 | 38.22 |

[a] 0 = None;
1 = Slight;
2 = Moderate;
3 = Severe.

TABLE VI

MEAN TREATMENT EFFECT OF ANTIOXIDANT CONCENTRATION ON GROWTH OF CORN SEEDLINGS

| | Height (cm) UR % | | Tissue Weight (gm) Fresh UR % | | Tissue Weight (gm) Dry UR % | | Leaf Area (cm$^2$) Non-Functional UR % | | Leaf Area (cm$^2$) Functional UR % | | Leaf Area (cm$^2$) Total UR % | |
|---|---|---|---|---|---|---|---|---|---|---|---|---|
| Antioxidant Content, % wt. | 95 | 84 | 95 | 84 | 95 | 84 | 95 | 84 | 95 | 84 | 95 | 84 |
| (Expt. No. 1) | | | | | | | | | | | | |
| 0 | 13.2 | 10.3 | 24.0 | 23.2 | 2.27 | 1.73 | 167 | 233 | 1046 | 548 | 1214 | 782 |
| 1 | 14.9 | 9.7 | 34.8 | 23.9 | 3.23 | 2.37 | 168 | 268 | 1310 | 584 | 1477 | 852 |
| 2 | 14.4 | 12.0 | 31.0 | 15.4 | 3.33 | 1.70 | 156 | 285 | 1223 | 696 | 1378 | 980 |
| 4 | 12.2 | 10.2 | 26.8 | 14.2 | 2.20 | 1.40 | 86 | 287 | 1030 | 552 | 1118 | 739 |
| 8 | 2.7 | 11.8 | 3.5 | 15.4 | 0.25 | 1.23 | 60 | 85 | 95 | 391 | 156 | 476 |
| S.E. ± | 1.40 | | 5.13 | | 0.57 | | 63.6 | | 141.4 | | 192.6 | |
| C.V. % | 21.8 | | 41.9 | | 49.6 | | 65.0 | | 32.8 | | 36.4 | |
| | UR % 72 | 60 | UR % 72 | 60 | UR % 72 | 60 | UR % 72 | 60 | UR % 72 | 60 | UR % 72 | 60 |
| (Expt. No.2) | | | | | | | | | | | | |
| 0 | 11.9 | 12.6 | 14.2 | 19.2 | 1.67 | 2.03 | 258 | 213 | 523 | 773 | 781 | 986 |
| 1 | 11.0 | 11.4 | 14.2 | 10.0 | 1.50 | 1.37 | 202 | 153 | 599 | 306 | 802 | 459 |
| 2 | 14.0 | 9.1 | 24.8 | 14.7 | 2.00 | 1.57 | 254 | 261 | 979 | 602 | 1233 | 863 |
| 4 | 14.0 | 11.5 | 19.4 | 19.6 | 1.93 | 2.43 | 219 | 310 | 807 | 746 | 1027 | 1055 |
| 8 | 7.9 | 13.5 | 17.6 | 26.4 | 2.30 | 3.10 | 170 | 346 | 548 | 1000 | 718 | 1246 |
| S.E. | 1.98 | | 5.79 | | 0.54 | | 62.5 | | 181.3 | | 215.3 | |
| C.V. % | 29.4 | | 55.7 | | 45.4 | | 47.4 | | 45.6 | | 40.7 | |

[a] Mixed alkylphenols containing 55% 2,4-dimethyl-6-tert. butylphenol.

What is claimed is:

1. A non-phytotoxic oxidation-inhibited horitcultural spray oil composition having a Gravity API of 31-50, a viscosity at 100° F. of 81 to 87 Saybolt Universal Seconds and a boiling range of 85 to 775° F. and a minimum unsulfonated residue of 85% and containing from 0.01 to 8 weight percent of at least one a nonphytotoxic, non-carcinogenic, anti-oxidant compound capable of substantially preventing the oxidation of unsaturated hydrocarbons and of aromatic compounds contained in said oil in the presence of sunlight; said compound being selected from the group consisting of oxidation inhibitors and compounds capable of preventing the homolytic decomposition of peroxides.

2. The invention as recited in claim 1, wherein said antioxidant is a mixture of alkylphenols.

3. The invention as recited in claim 2, wherein said mixture contains a major portion of 2,4-dimethyl-6-tertiary butylphenol.

4. The invention as recited in claim 1, wherein said anti-oxidant is selected from the group of N,N'-di-sec. butyl-p-phenylenediamine; phenyl-a-naphthyl amine; p,p'-dioctyldiphenylamine; diphenylamine, β-naphthylamine, 2-mercaptobenzothiazole, zinc dibutyldithio carbamate, sulfurized sperm oil and mixtures thereof.

5. The invention as recited in claim 1, wherein the higher stated amount of antioxidant is used with oils having a lower unsulfonated residue.

* * * * *